United States Patent
Rowe et al.

(10) Patent No.: US 10,300,052 B2
(45) Date of Patent: May 28, 2019

(54) METHODS FOR INCREASING CFTR ACTIVITY

(71) Applicant: THE UAB RESEARCH FOUNDATION, Birmingham, AL (US)

(72) Inventors: Steven M Rowe, Birmingham, AL (US); Mark Dransfield, Homewood, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/582,260

(22) Filed: Apr. 28, 2017

(65) Prior Publication Data

US 2017/0266177 A1    Sep. 21, 2017

Related U.S. Application Data

(62) Division of application No. 14/387,818, filed as application No. PCT/US2013/032268 on Mar. 15, 2013, now abandoned.

(60) Provisional application No. 61/621,043, filed on Apr. 6, 2012.

(51) Int. Cl.
*A61K 31/47* (2006.01)

(52) U.S. Cl.
CPC ..................................... *A61K 31/47* (2013.01)

(58) Field of Classification Search
CPC ....... A61K 31/47; A61K 31/192; A61K 35/42
See application file for complete search history.

(56) References Cited

U.S. PATENT DOCUMENTS

| | | | | |
|---|---|---|---|---|
| 2010/0256184 A1 | 10/2010 | Rowe | | |
| 2011/0230519 A1* | 9/2011 | Arekar | ................. | C07D 215/56 514/312 |

FOREIGN PATENT DOCUMENTS

| | | |
|---|---|---|
| WO | 2010019239 | 2/2010 |
| WO | 2011115778 | 9/2011 |
| WO | 2012158885 | 11/2012 |

OTHER PUBLICATIONS

Mou Xiaofen, "Advances in Research on the Pathogenesis of Cystic Fibrosis," Section of Respiratory System Foreign Medical Sciences, 2002, vol. 22, No. 2 pp. 86-87.
Bonnie W. Ramsey, et al., A CFTR Potentiator in Patients with Cystic Fibrosis and the G551D Mutation, N. Engl J Med., vol. 365, No. 18, Nov. 3, 2018, pp. 1663-1672.
Fredrick Van Goor, et al., Rescue of CF airway epithelial cell function in vitro by a CFTR potentiator, VX-770, PNAS, vol. 106, No. 44, Nov. 3, 2009, pp. 18825-18830.
I Liu, et al., Modulation of Ion Transport & Mucus Clearance in Cells & Tissues: New Insights from Video-Rate Reflectance Tomography Imaging, 24th Annual North American Cystic Fibrosis Conference, Oct. 2010, abstract 222, pp. 297-298.

\* cited by examiner

*Primary Examiner* — Pancham Bakshi
(74) *Attorney, Agent, or Firm* — Thomas G. Peterson; Maynard Cooper & Gale

(57) ABSTRACT

The present disclosure provides compounds effective in increasing mucociliary clearance in a subject. In one embodiment, the compounds are of the general formula I. The present disclosure further shows that such compounds are effective in increasing activation of the CFTR, thereby increasing mucociliary clearance in the subject. The present disclosure further shows that such compounds are effective in increasing the depth of ASL, thereby increasing mucociliary clearance in the subject. In one embodiment of each of the foregoing, the subject is free from congenital or genetic defect in the cellular mucociliary clearance apparatus and/or acquired abnormality in the cellular mucociliary clearance apparatus.

16 Claims, 8 Drawing Sheets
(4 of 8 Drawing Sheet(s) Filed in Color)

METHODS FOR INCREASING CFTR ACTIVITY

FIELD OF THE DISCLOSURE

The present disclosure relates to methods of augmenting mucociliary clearance in a subject. In a specific embodiment, the present disclosure relates to methods of augmenting mucociliary clearance in a subject wherein the subject is free from a congenital or genetic defect in the cellular mucociliary clearance apparatus and/or an acquired abnormality in the cellular mucociliary clearance apparatus.

BACKGROUND

Disorders of mucus clearance (mucous stasis) and increased mucous production are common problems that impact a variety of human conditions. This is true even in the setting of normal epithelial function and a normally functioning cellular mucociliary clearance apparatus whereupon mucociliary clearance is suboptimal for the particular condition. A number of diseases and/or conditions may lead to suboptimal mucous clearance and/or excess mucous production. In such situations, mucociliary clearance may be considered impaired even though no defects or abnormalities exist in the cellular mucociliary clearance apparatus as the normal functioning cellular mucociliary apparatus is not sufficient given the underlying condition of the patient.

For example, individuals with neuromuscular weakness caused by congenital or genetic conditions, such as, but not limited to, muscular dystrophy, spinal muscular atrophy, and ALS, suffer from recurrent pneumonia due to poor cough clearance which leads to mucous stasis. In addition, individuals with acquired anatomic problems resulting in muscular weakness, such as but not limited to, paraplegia, quadriplegia, diaphragmatic paralysis and the like, suffer the same fate. Other subjects, such as those suffering from excess mucous production due to conditions such as, but not limited to, asthma and status asthmaticus, those suffering from impaired immunity due to conditions such as, but not limited to, immunoglobulin deficiency, SCID, hyper-IgE syndrome, and similar conditions, those suffering from anatomic respiratory abnormalities impairing mucus clearance, and those suffering from recurrent pneumonia for unclear causes and those suffering from oropharyngeal abnormalities, suffer from atelectasis and/or pneumonia due to excess mucus production that overwhelms the capacity of the mucociliary clearance apparatus to transport it effectively. These disorders due to or resulting in suboptimal mucous clearance and/or excess mucous production are a serious recurrent problem causing considerable morbidity and are also a contributing cause to mortality. Thus even in diseases where mucociliary clearance is normal, enhancement of mucociliary clearance to supernormal levels is beneficial to combat particular diseases.

The art is lacking compounds and treatment methods to augment mucociliary clearance and/or airway epithelial cell function. The art is particularly lacking compounds and treatment methods to enhance mucociliary clearance and/or airway epithelial cell function in subjects that do not have a congenital or genetic defect in the cellular mucociliary clearance apparatus and/or an acquired abnormality in the cellular mucociliary clearance apparatus. Such compounds and treatment methods would offer substantial benefits to those subjects by treating conditions arising from suboptimal mucous clearance and/or excess mucous production and similar conditions.

The present disclosure provides a solution to the problems encountered in the art by providing compounds and treatment methods to enhance mucociliary clearance and/or airway epithelial cell function to overcome suboptimal mucous clearance and/or excess mucous production. In addition, the present disclosure provides a solution to the problems encountered in the art by providing compounds and treatment methods to induce supra-normal mucociliary clearance to enhance mucociliary clearance and/or airway epithelial cell function to overcome suboptimal mucous clearance and/or excess mucous production. Furthermore, the present disclosure provides the foregoing benefits in a subject wherein the subject is free from a congenital or genetic defect in the cellular mucociliary clearance apparatus and/or an acquired abnormality in the cellular mucociliary clearance apparatus. In one embodiment, the suboptimal mucous clearance and/or increased mucous production is due to or associated with neuromuscular diseases, anatomic respiratory abnormalities, acquired anatomic problems resulting in muscular weakness, anatomic weakness, asthma and status asthmaticus, relative susceptibility to respiratory infection (such as due to impaired immunity), and/or excess mucous production.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A shows CFBE41o-cells with and without complementary expression of wild type CFTR were grown at air-liquid interface, then mounted in Ussing chambers and stimulated with ivacaftor (VX-770; 10 µM) or vehicle control following amiloride (100 µM) and forskolin (100 nM) in the setting of a Cl-secretory gradient. CFBE41o-cells complemented by stable expression of WT-CFTR (by a lentivirus promoter) are shown in comparison to CFBE41o-cells without WT CFTR complementation (parental cells). *P<0.05, **P<0.005, n=5/condition.

FIG. 1B shows representative Isc tracings of cells were sequentially exposed to forskolin (100 nM) and ivacaftor (VX-770; 10 µM) or vehicle control, followed by CFTR Inh-172 (10 µM) in the setting of amiloride (100 µM).

FIG. 2A shows representative Z-scan confocal images derived from the surface of HBE cells following exposure to vehicle control or ivacaftor (VX-770; 10 µM) to the basolateral compartment for 24 h prior to assay. White scale bars designate 10 µm.

FIG. 2B shows summary data from experiments shown in FIG. 2A. **P<0.005, n=10/condition. Dotted line indicates ASL depth of a panel of CF HBE cells using the exact same method.

FIG. 2C shows mucociliary transport rates derived from HBE cells. ivacaftor (VX-770; 10 µM) or vehicle control was added to basolateral compartment of monolayers co-stimulated with the cAMP agonist VIP (30 nM) immediately after the time=0 h measurement. **P<0.001 vs. vehicle control, n=10 particles/condition.

FIG. 2D shows representative SD-OCT images of fully-differentiated HBE cells were exposed to CSE (2%) or vehicle (media with 2% DMSO) apically and VX-770 (10

μM) or vehicle (0.1% DMSO) basolaterally for 24 hrs. ASL depth is shown as red bar. White scale bar=10 μm.

Figure 3A:
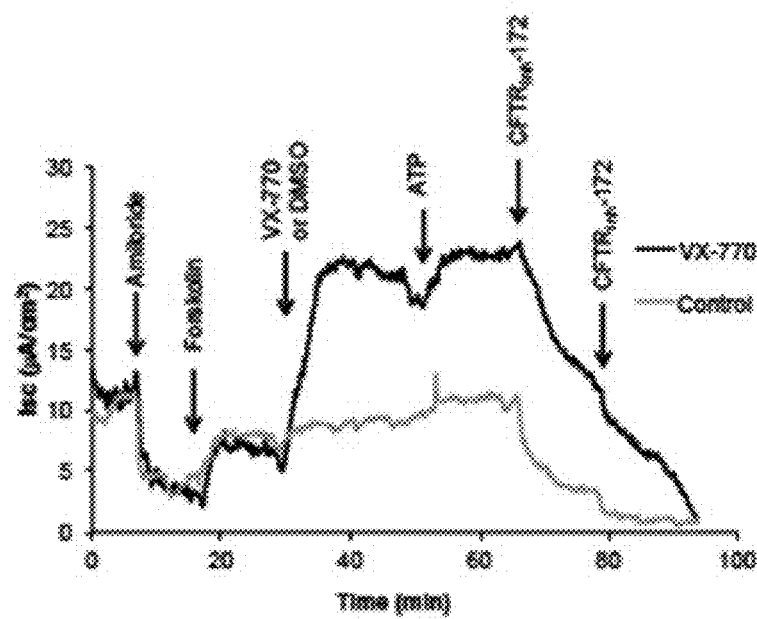
Figure 3B:
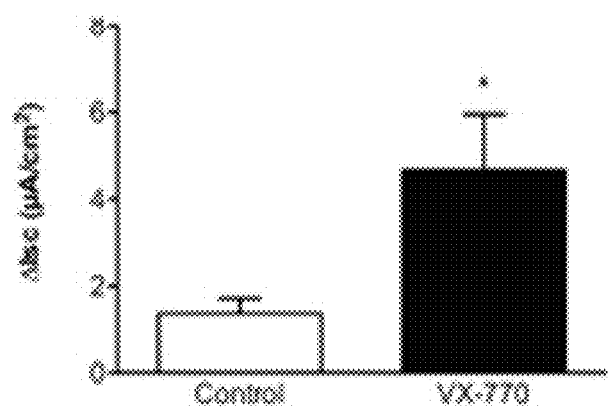

FIGS. 3A-3B show the CFTR potentiator ivacaftor augments wild-type CFTR activity.

FIG. 3A shows representative Isc tracing of bronchus derived from a normal human subject following dissection of the mucosal layer that was then mounted in an Ussing chamber under voltage clamp conditions and bathed in symmetric Ringer's solution. Serial addition of amiloride (100 μM), forskolin (100 nM), and ivacaftor (VX-770; 10 μM) or vehicle control is shown, followed by addition of ATP (10 μM), and CFTR Inh-172 (10 μM×2) as control additions.

FIG. 3B shows summary data derived from experiments shown in FIG. 3A. The change in Isc following addition of ivacaftor (VX-770) or vehicle control is shown. *$P<0.05$, n=19, 24 samples/condition.

FIGS. 4A-4D show the effects of CFTR activators on airway epithelial function in human bronchial epithelial cells by μOCT. Control HBE cells containing a defective CFTR (designated control, CF) and HBE cells containing a WT-CFTR (designated control and VX-770, wild-type) received vehicle alone (control; 0.2% DMSO) or ivacaftor (10 μM). FIGS. 4A-4D show ASL depth (FIG. 4A), PCL depth (FIG. 4B), cilia beat frequency (FIG. 4C), and mucociliary transport (MCT) rate (FIG. 4D) as quantified from μOCT images.

Figure 5A:
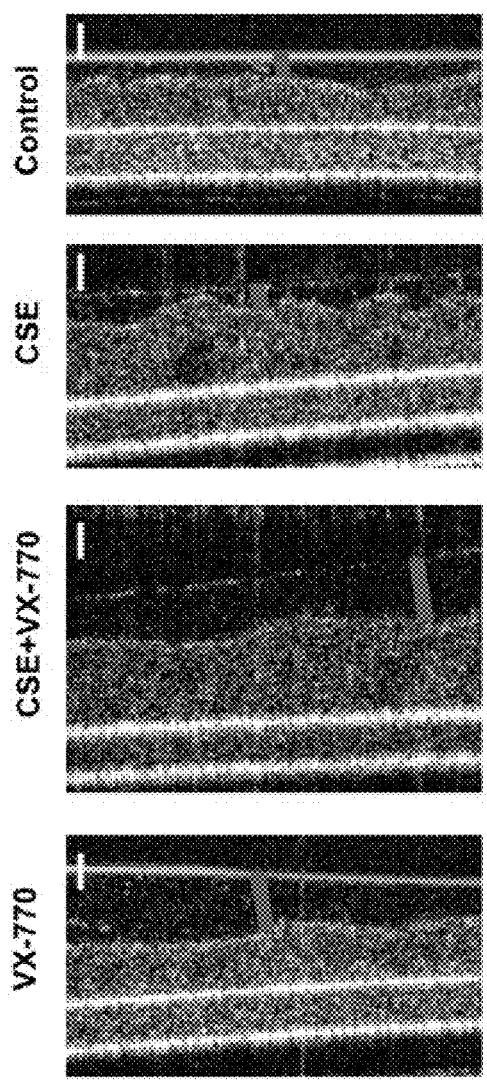
Figure 5B:
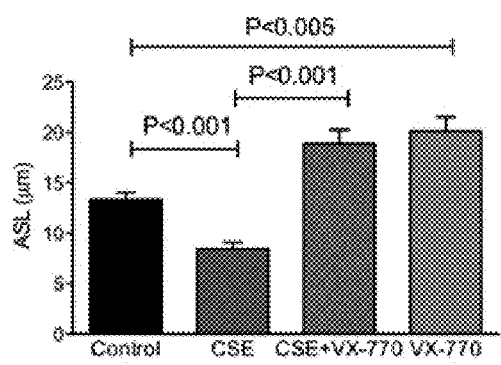
Figure 5C:
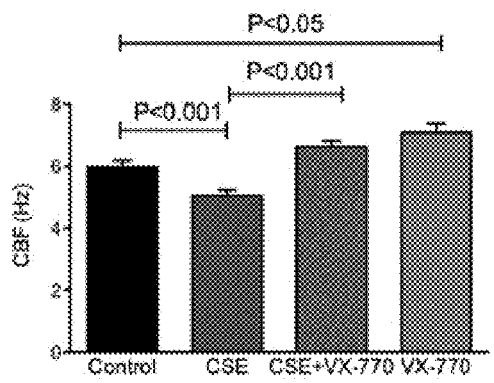
Figure 5D:
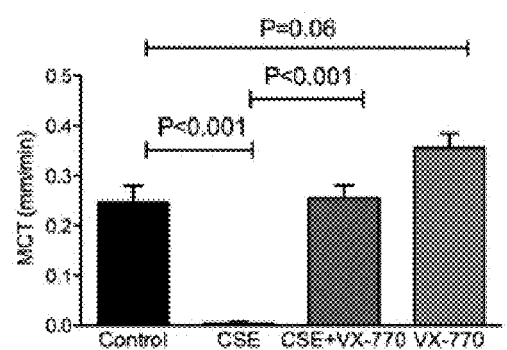

FIGS. 5A-5D show the effects of CFTR activators on airway epithelial function in human bronchial epithelial cells by μOCT. FIG. 5A shows representative μOCT images of fully-differentiated HBE cells were exposed to vehicle (control; media with 2% DMSO), CSE (2%), CSE (2%) and ivacaftor (10 μM) or ivacaftor alone (10 μM; 0.1% DMSO). CSE was applied apically and ivacaftor basolaterally. Cells were exposed to each condition for 24 hrs. ASL depth is shown as a dark bar. White scale bar=10 μm. FIGS. 5B-5D show ASL depth (FIG. 5B), cilia beat frequency (FIG. 5C), and mucociliary transport (MCT) rate (FIG. 5D) as quantified from μOCT images. Data are derived from 5 measures per well, and 3 wells per condition.

Figure 6A:
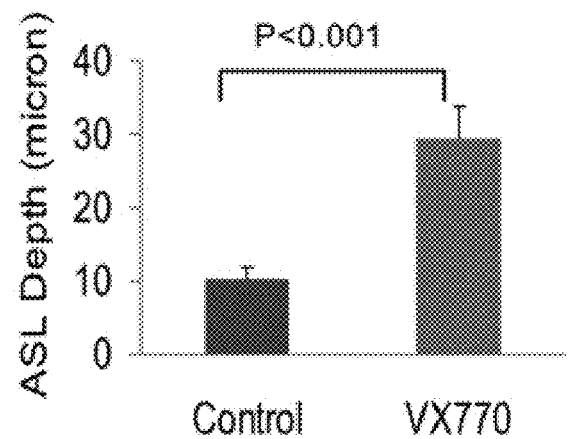
Figure 6B:
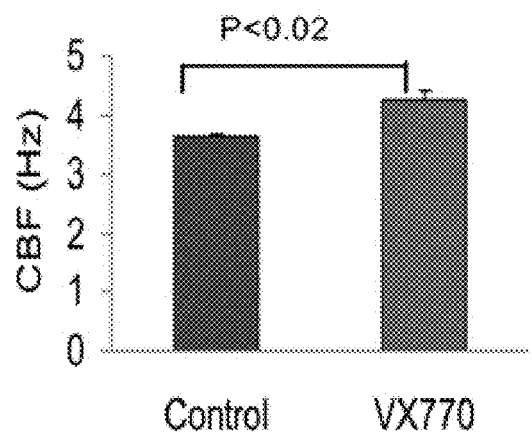
Figure 6C:
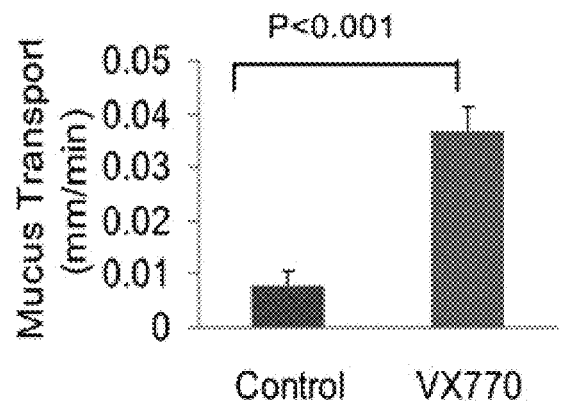

FIGS. 6A-6C show the effects of CFTR activators on airway epithelial function in human bronchial tissue by μOCT. FIGS. 6A-6C show ASL depth (FIG. 6A), CBF (FIG. 6B) and MCT (FIG. 6C), respectively in response to ivacaftor treatment (10 μM).

Figure 7A:
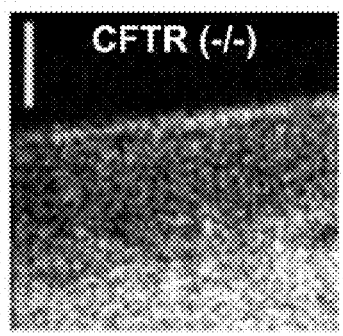
Figure 7B:
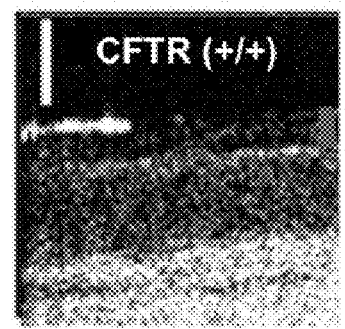
Figure 7C:
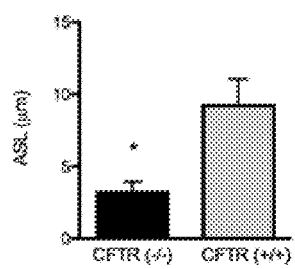
Figure 7E:
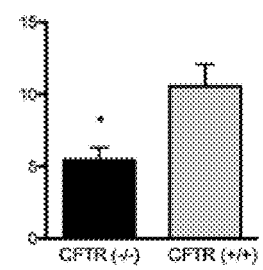
Figure 7G:
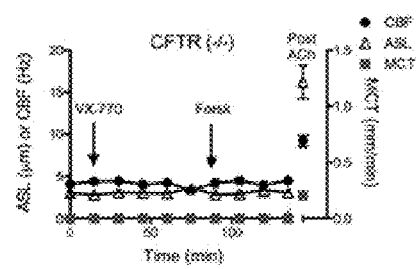
Figure 7D:
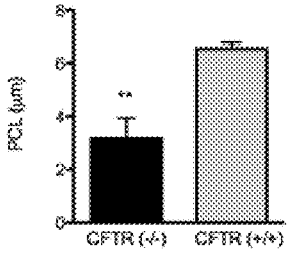
Figure 7F:
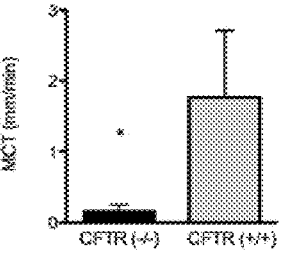
Figure 7H:
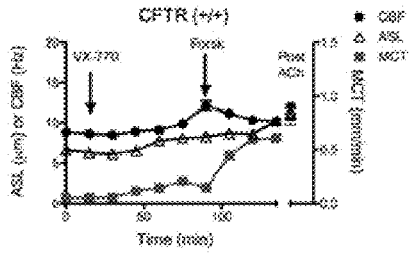

FIGS. 7A-7H show the effects of CFTR activators on airway epithelial function in intact porcine trachea by μOCT. FIGS. 7A-7B show representative μOCT images for a CFTR−/− (FIG. 7A) and CFTR+/+ (FIG. 7B) animal. FIGS. 7C-7F, respectively, show ASL depth (FIG. 7C), PCL depth (FIG. 7D), CBF (FIG. 7E) and MCT (FIG. 7F) measurements derived from μOCT images from CFTR−/− and CFTR+/+ animals. FIGS. 7G and 7H show the response of epithelial functional parameters, namely ASL depth and MCT in CFTR−/− (FIG. 7G) and CFTR+/+(FIG. 7H) animals in response to sequential pharmacologic intervention by ivacaftor (10 μM), forskolin (100 nM) and acetylcholine (100 μM).

DETAILED DESCRIPTION

Mucociliary transport and the function of the airway surface is an area of active study of the human respiratory system. In healthy airways, a layer of cilia continuously transports airway mucus, a vital mechanism for defense against particulate contamination and biological invaders.

Defects in mucociliary clearance are known in the art. One common example is cystic fibrosis (CF). CF is caused by mutations in the cystic fibrosis transmembrane conductance regulator (CFTR). The CFTR is an epithelial anion channel expressed predominantly in exocrine tissues. Mutations in the gene encoding CFTR are the proximate cause of CF. In the lung, loss of CFTR function results in airway surface liquid (ASL) depletion, thickened mucous, reduced mucociliary clearance, chronic bacterial infection, and excess inflammation. Over time, pulmonary obstruction due to inspissated respiratory secretions and bronchiectasis ensues, resulting in respiratory failure.

CF and other conditions affecting mucociliary clearance are caused by congenital defects in the mucociliary clearance apparatus, such as, but not limited to, the CFTR. Compounds are known in the art that increase the activity of CFTR in subjects with congenital defects in the CFTR.

However, the present disclosure is based on the enhancement of mucociliary clearance and/or airway epithelial cell function in a subject with suboptimal mucous clearance and/or excess mucous production and on the enhancement of mucociliary clearance and/or airway epithelial cell function in a subject with suboptimal mucous clearance and/or excess mucous production in a subject wherein the subject is free from congenital or genetic defect in the cellular mucociliary clearance apparatus and/or acquired abnormality in the cellular mucociliary clearance apparatus. As a result, the function of the mucociliary clearance apparatus is improved.

Increasing or enhancing the activity of the cellular mucociliary clearance apparatus has important clinical significance, even among individuals without congenital or genetic defect in the cellular mucociliary clearance apparatus and/or acquired abnormality in the cellular mucociliary clearance apparatus. One important member of the cellular mucociliary clearance apparatus is the CFTR. As discussed above, mutations in the CFTR can lead to suboptimal mucous clearance. In one embodiment, the present disclosure employs compounds that increase the activity and/or function of the CFTR in subjects without congenital or genetic defect and/or acquired abnormality in the CFTR to enhance mucociliary clearance in a subject. In one embodiment, mucociliary clearance is enhanced to supernormal levels. Recently, the CFTR potentiator ivacaftor (Kalydeco™, VX-7.70) was recently approved for use in CF patients with the G551D-CFTR gating mutation based on marked improvements in phase 2 and 3 trials (Ramsey B W, et al., *The New England Journal of Medicine* 2011; 365:1663-1672; Accurso F J, et al., *N Engl J Med* 2010; 363:1991-2003). Ivacaftor robustly enhances anion secretion by potentiating cAMP mediated CFTR channel gating (Van Goor, F. et al., *Proc Natl Acad Sci USA* 2009; 106:18825-18830) leading to increased airway fluid secretion.

The present disclosure is based on enhancing mucociliary clearance and/or airway epithelial cell function in a subject by increasing the activity of a component of the cellular mucociliary clearance apparatus in a subject. In one embodiment, the component of the cellular mucociliary clearance apparatus is the CFTR. In one embodiment, the subject free from congenital or genetic defects in the cellular mucociliary clearance apparatus. In another embodiment, the subject is free from an acquired abnormality in the cellular mucociliary clearance apparatus. In another embodiment, the subject is free from congenital or genetic defects in the cellular mucociliary clearance apparatus and an acquired abnormality in the cellular mucociliary clearance apparatus.

In one embodiment, the suboptimal mucociliary clearance in a subject is due to or associated with a neuromuscular disease. Neuromuscular disease may be caused by or associated with congenital or acquired genetic conditions, such as, but not limited to, muscular dystrophy, spinal muscular atrophy, ALS.

In another embodiment, the suboptimal mucociliary clearance in a subject is due to or associated with an acquired anatomic problem resulting in muscular weakness. Such acquired anatomic problems resulting in muscular weakness may be caused by or associated with conditions, such as, but not limited to, paraplegia, quadriplegia, and diaphragmatic paralysis.

In still another embodiment, the suboptimal mucociliary clearance in a subject is due to or associated with excess mucous production. Such excess mucous production may be caused by or associated with conditions, such as, but not limited to, asthma and asthmaticus.

In still another embodiment, the mucociliary clearance in a subject is normal but the subject suffers increased prevalence of respiratory infections due to immune deficiency. Risk of respiratory infection could be reduced by enhancement of mucociliary clearance.

In any of the foregoing embodiment, the subject is free from a congenital or genetic defect in the cellular mucociliary clearance apparatus and/or an acquired abnormality in the cellular mucociliary clearance apparatus. In one embodiment of the foregoing, mucociliary clearance is enhanced to supranormal levels. In one embodiment of the foregoing, an acquired abnormality in the cellular mucociliary clearance apparatus may be due to environmental factors, such as, but not limited to, smoking or chronic obstructive pulmonary disease.

Compounds

Compounds useful in the methods disclosed herein include any known activators of the cellular mucociliary clearance apparatus. In one embodiment, such activators are CFTR activator compounds. In one embodiment, the CFTR activator is a CFTR potentiator. Known CFTR potentiators include, but are not limited to, are anthracene-9-carboxylic acid (9-Anthroic acid), phloxine B, benzimidazolone analogs NS004 and NS1619, genistein, 7-n-Butyl-6-(4-hydroxyphenyl)[5H]pyrrolo[2,3-b]pyrazine (aloisine A), 2-(2-(1H-indol-3-yl)-N-methylacetamido)-N-(4-isopropylphenyl)-2-phenylacetamide (PG01), N-cycloheptyl-6-(N-ethyl-N-phenylsulfamoyl)-4-oxo-1,4-dihydroquinoline-3-carboxamide (SF01), sulfonamide 6-(N-ethyl-N-phenylsulfamoyl)-N-(2-methoxybenzyl)-4-oxo-1,4-dihydroquinoline-3-carboxamide (SF03), capsaicin and curcumin.

In one embodiment, the compound is a compound of the general formula I below.

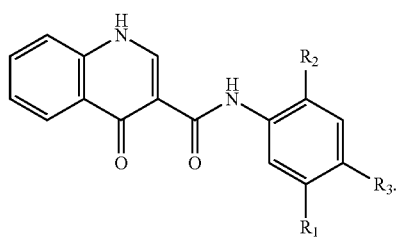

I

In this structure, $R_2$ and $R_3$ are each independently, H, OH or substituted or unsubstituted C1-C7 alkyl chains and $R_1$ is OH or H.

As used herein, the term "alkyl", whether used alone or as part of a substituent or linking group, includes straight hydrocarbon groups comprising from one to 4 carbon atoms. Thus the phrase includes straight chain alkyl groups such as methyl, ethyl, propyl and the like. The phrase also includes branched chain isomers of straight chain alkyl groups, including but not limited to, the following which are provided by way of example: —CH(CH$_3$)$_2$, —C(CH$_3$)$_3$, CH(CH$_3$)(CH$_2$CH$_3$), —CH(CH$_2$CH$_3$)$_2$, and others. The phrase also includes cyclic alkyl groups such as cyclopropyl and cyclobutyl.

In one embodiment, each of $R_2$ and $R_3$ is —C(CH$_3$)$_3$ and $R_1$ is OH.

In a specific embodiment, the compound is ivacaftor (VX-770), and has the structure shown in II.

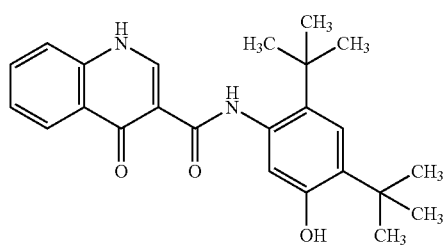

II

In one embodiment, the CFTR activator compound is a CFTR potentiator. In another embodiment, the CFTR activator compound is a compound of the general formula I. In still another embodiment, the CFTR activator compound is ivacaftor (VX-770).

In another embodiment the CFTR activator compound is roflumilast and other PDE analogues that activate CFTR through elevation of cAMP.

In another embodiment, the CFTR activator is a flavonoid such as an isoflavone (e.g. genistein, quercetin, etc.)

In another embodiment, the CFTR activator is an agonist of cAMP or PKA.

In another embodiment, the agent could activate other modulators of anion transport, such as calcium activated chloride channels.

Methods of Treatment

The present disclosure shows that activators of the cellular mucociliary clearance apparatus, such as but not limited to, a CFTR activator, are effective in enhancing mucociliary clearance and/or airway epithelial cell function in a subject. Therefore, such compounds are effective in treating suboptimal mucociliary clearance in a subject. In one embodiment, such compounds are compounds of the general formula I. The present disclosure further shows that compounds effective in increasing activity and/or function of the CFTR are effective in enhancing mucociliary clearance and/or airway epithelial cell function in a subject, thereby increasing mucociliary clearance in the subject. The foregoing benefits are achieved even in cases where the mucociliary apparatus is considered to function normally. In one embodiment, such compounds induce mucociliary clearance to supernormal levels in a subject through enhancement of a component of the mucociliary clearance apparatus.

The present disclosure further shows that such compounds are effective in increasing a parameter of airway epithelial cells function. Relevant parameters of airway epithelial cell function include, but are not limited to, depth of airway surface liquid (ASL), depth of periciliary liquid (PCL), ciliary beat frequency (CBF) and rate of mucociliary transport (MCT). In one embodiment, a single parameter of airway epithelial cell function is increased. In an alternate embodiment, two or more parameters of airway epithelial cell function are increased. In an alternate embodiment, three or more parameters of airway epithelial cell function are increased. In an alternate embodiment, all four more parameters of airway epithelial cell function are increased. In a particular embodiment, the rate of MCT is increased. In a particular embodiment, the depth of ASL is increased. In a particular embodiment, depth of the ASL and the rate of MCT are increased. In another particular embodiment, depth of the ASL, CBF and the rate of MCT are increased. In another particular embodiment, depth of the ASL, depth of PCL and the rate of MCT are increased. In another particular embodiment, depth of the ASL, depth of PCL, CBF and the rate of MCT are increased. In another particular embodiment, mucus viscosity is improved (i.e., decreased) as a result of increasing a parameter of airway epithelial cell function. In certain embodiments, mucous viscosity is improved without a noticeable difference or corresponding improvement in an airway epithelial cell parameter, such as depth of ASL, depth of PCL or CBF. Improvements in mucus viscosity may result from augmenting fluid and/or bicarbonate transfer via the CFTR or calcium activated chloride channels.

As a result of increasing one or more parameters of airway epithelial cell function, mucociliary clearance in the subject is enhanced. In one embodiment, mucociliary clearance is enhanced to supernormal levels. In one embodiment of each of the foregoing, the subject is free from congenital or genetic defect in the cellular mucociliary clearance apparatus. In one embodiment of the foregoing, the subject is free from a congenital or genetic defect in the CFTR. In one embodiment of the foregoing, the subject is free from an acquired abnormality in the cellular mucociliary clearance apparatus. In one embodiment of the foregoing, the subject is free from an acquired abnormality in the CFTR.

In one embodiment, the present disclosure provides methods for treating suboptimal mucociliary clearance in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases a parameter of airway epithelial cell function. In one aspect of this embodiment, such parameter is depth of ASL, depth of PCL, CBF, rate of MCT or any combination of the foregoing. In another aspect such parameter is depth of ASL, rate of MCT or a combination of the foregoing.

In another embodiment, the present disclosure provides methods for increasing mucociliary clearance in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases a parameter of airway epithelial cell function. In one aspect of this embodiment, such parameter is depth of ASL, depth of PCL, CBF, rate of MCT or any combination of the foregoing. In another aspect such parameter is depth of ASL, rate of MCT or a combination of the foregoing.

In another embodiment, the present disclosure provides methods for increasing the activity of the CFTR in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment of this method, such administration enhances mucociliary clearance in a subject. In another embodiment of this method, such administration enhances mucociliary clearance in a subject to supernormal levels. In still another embodiment of this method, such administration increases a parameter of airway epithelial cell function. In one aspect of this embodiment, such parameter is depth of ASL, depth of PCL, CBF, rate of MCT or any combination of the foregoing. In another aspect such parameter is depth of ASL, rate of MCT or a combination of the foregoing.

In another embodiment, the present disclosure provides methods for improving mucus viscosity (i.e., decreased mucus viscosity) in a subject. Such method comprises the step of administering to the subject an amount of an activator compound capable of enhancing the activity of the cellular mucociliary clearance apparatus. Methods for determining viscosity of mucus are known in the art and include in suit fluorescence after photobleaching and particle tracking microrheology. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In one embodiment of this method, mucus viscosity is improved as a result of increasing a parameter of airway epithelial cell function, such as, but not limited to, depth of ASL, depth of PCL, CBF and rate of MCT. In one embodiment of this method, mucous viscosity is improved without a noticeable difference or corresponding improvement in an airway epithelial cell parameter, such as depth of ASL, depth of PCL or CBF. In such embodiment, improvements in mucus viscosity may result from augmenting fluid and/or bicarbonate transfer via the activation of the CFTR or calcium activated chloride channels.

In another embodiment, the present disclosure provides methods for enhancing a parameter of airway epithelial cell function in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In one aspect of this embodiment, such parameter is depth of ASL, depth of PCL, CBF, rate of MCT or any combination of the foregoing. In another aspect such parameter is increasing the depth of ASL. In yet another aspect such parameter is increasing the rate of MCT. In still a further aspect, such parameter is increasing the depth of ASL and increasing the rate of MCT. In still a further aspect, such parameter is increasing the depth of ASL, increasing the depth of PCL, increasing CBF, increasing the rate of MCT or a combination of the foregoing.

In another embodiment, the present disclosure provides methods for increasing the rate of MCT in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases the rate of MCT as well as increases in addition to another parameter of airway epithelial cell function. In one aspect of this embodiment, such parameter is depth of ASL, depth of PCL, CBF or any combination of the foregoing. In another aspect such parameter is depth of ASL.

In another embodiment, the present disclosure provides methods for increasing the depth of ASL in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases the depth of ASL as well as increases in addition to another parameter of airway epithelial cell function. In one aspect of this embodiment, such parameter is depth of PCL, CBF, rate of MCT or any combination of the foregoing. In another aspect such parameter is rate of MCT.

In another embodiment, the present disclosure provides methods for increasing the depth of PCL in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases the depth of PCL as well as increases in addition to another parameter of airway epithelial cell function. In one aspect of this embodiment, such parameter is depth of ASL, CBF, rate of MCT or any combination of the foregoing. In another aspect such parameter is depth of ASL, rate of MCT or a combination of the foregoing.

In another embodiment, the present disclosure provides methods for increasing CBF in a subject. Such method comprises the step of administering to the subject an amount of an activator compound capable of enhancing the activity of the cellular mucociliary clearance apparatus. In one embodiment, such activator compound is a CFTR activator or a pharmacologically acceptable salt thereof. In one embodiment, such administration enhances the activity and/or function of the CFTR. In another embodiment, the activator compound activates, directly or indirectly, other anion transport mechanisms, such as, but not limited to, calcium activated chloride channels. In another embodiment of this method, such administration enhances mucociliary clearance in a subject. In another embodiment of this method, such administration enhances mucociliary clearance in a subject to supernormal levels. In still another embodiment of this method, such administration increases CBF as well as increases in addition to another parameter of airway epithelial cell function. In one aspect of this embodiment, such parameter is depth of ASL, depth of PCL, rate of MCT or any combination of the foregoing. In another aspect such parameter is depth of ASL, rate of MCT or a combination of the foregoing.

In one aspect of the foregoing methods, the subject is free from congenital or genetic defects in the cellular mucociliary clearance apparatus. In another aspect of the foregoing methods, the subject is free from an acquired abnormality in the cellular mucociliary clearance apparatus. In still another aspect of the foregoing methods, the subject is free from congenital or genetic defects in the cellular mucociliary clearance apparatus and an acquired abnormality in the cellular mucociliary clearance apparatus. In still another aspect of the foregoing methods, the subject is free from a congenital or genetic defect in the CFTR. In still another aspect of the foregoing methods, the subject is free from an acquired abnormality in the CFTR.

In one aspect of the foregoing methods, suboptimal mucociliary clearance in a subject is due to or associated with a neuromuscular disease. Neuromuscular disease may be caused by or associated with congenital or acquired genetic conditions, such as, but not limited to, muscular dystrophy, spinal muscular atrophy, ALS.

In another aspect of the foregoing methods, the suboptimal mucociliary clearance in a subject is due to or associated with an acquired anatomic problem resulting in muscular weakness. Such acquired anatomic problems resulting in muscular weakness may be caused by or associated with conditions, such as, but not limited to, paraplegia, quadriplegia, and diaphragmatic paralysis.

In still another aspect of the foregoing methods, the mucociliary clearance in a subject is normal but suffers increased prevalence of respiratory infections due to immune deficiency. Risk of respiratory infection could be reduced by augmentation of mucociliary clearance.

In yet another aspect of the foregoing methods, the suboptimal mucociliary clearance in a subject is due to or associated with excess mucous production. Such excess mucous production may be caused by or associated with conditions, such as, but not limited to, asthma and asthmaticus.

In still a further aspect of the foregoing methods, the suboptimal mucociliary clearance in a subject is due to or associated with environmental factors. Such environmental factors include, but are not limited to, smoking.

In one aspect of the foregoing methods, the compound is a CFTR activator compound. In another aspect of the foregoing methods, the CFTR activator is a CFTR potentiator. In still another aspect of the foregoing methods, the CFTR activator compound is a compound of the compounds of the general formula I. In yet another aspect of the foregoing methods, the CFTR activator compound is ivacaftor (VX-770). In another aspect of the foregoing methods, the CFTR activator is a cAMP elevating agonist, such as, but not limited to, roflumilast. In another aspect of the foregoing methods, the CFTR activator compound is a PDE analogue that activates CFTR through elevation of cAMP. In another aspect of the foregoing methods, the CFTR activator is a flavonoid such as, but not limited to, an isoflavone. Suitable isoflavones include, but are not limited to, genistein, and quercetin. In another aspect of the foregoing methods, the CFTR activator is an agonist of cAMP or PKA. In another aspect of the foregoing methods, the compound activates other anion transports, such as, but not limited to, calcium activated chloride channels.

In still another aspect of the foregoing methods, the compound may administered alone or as a part of a pharmaceutical composition as described herein. A single compound of the present disclosure may be administered or multiple compounds of the present disclosure may be administered. In one aspect of this embodiment, the compound is a compound of the general formula I. Furthermore, in still another aspect of the foregoing methods, the compound administered is ivacaftor (VX-770).

In still another aspect of the foregoing methods, the subject is determined to be in need of such treatment. In still another aspect of the foregoing methods, the compound is administered in a therapeutically effective amount.

In yet another aspect of the foregoing methods, the subject may be a mammal. In certain embodiments, the subject is a human.

In still another aspect of the foregoing methods, the subjects treated can be further treated with one or more additional active agents. The one or more additional active agents and the compounds described herein or pharmaceutically acceptable salts or prodrugs thereof, can be administered together in a single composition or in separate compositions in any order, including simultaneous administration, as well as temporally spaced on the order of up to several days apart. The methods can also include more than a single administration of the one or more additional active agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

In still another aspect of the foregoing methods, the compounds of the present disclosure are administered at a dose of 75-750 mg/day. The compounds of the present disclosure may be administered once per day, twice per day or more than twice per day. In one embodiment, the compound is ivacaftor (VX-770) and the compound is administered 1-2 times per day for a total dose of 300 mg/day.

Pharmaceutical Compositions

Pharmaceutical compositions are provided that comprise an amount of a compound of the present disclosure. In one embodiment, such pharmaceutical compositions contain a therapeutically effective amount of a compound. In a particular embodiment, the compound is a compound of the general formula I, such as, but not limited to, ivacaftor (VX-770). In addition, other active agents may be included in such pharmaceutical compositions. Additional active agents to be included may be selected based on the disease or condition to be treated.

The pharmaceutical compositions disclosed may comprise one or more compound of the present disclosure, alone or in combination with additional active agents, in combination with a pharmaceutically acceptable carrier. Examples of such carriers and methods of formulation may be found in Remington: The Science and Practice of Pharmacy ($20^{th}$ Ed., Lippincott, Williams & Wilkins, Daniel Limmer, editor). Such pharmaceutical compositions may be used in the manufacture of a medicament for use in the methods of treatment and prevention described herein. The compounds of the disclosure are useful in both free form and in the form of pharmaceutically acceptable salts.

The pharmaceutically acceptable carriers described herein, including, but not limited to, vehicles, adjuvants, excipients, or diluents, are well-known to those who are skilled in the art. Pharmaceutically acceptable excipients are also well-known to those who are skilled in the art. The choice of excipient will be determined in part by the particular compound(s), as well as by the particular method used to administer the composition. Accordingly, there is a wide variety of suitable formulations of the pharmaceutical composition of the present invention. The following methods and excipients are merely exemplary and are in no way limiting. Suitable carriers and excipients include solvents such as water, alcohol, and propylene glycol, solid absorbents and diluents, surface active agents, suspending agent, tableting binders, lubricants, flavors, and coloring agents. The pharmaceutically acceptable carriers can include polymers and polymer matrices. Typically, the pharmaceutically acceptable carrier is chemically inert to the active agents in the composition and has no detrimental side effects or toxicity under the conditions of use.

The compounds of the present disclosure and pharmaceutical compositions containing such compounds as described in the instant disclosure can be administered by any conventional method available for use in conjunction with pharmaceuticals, either as individual therapeutic agents or in combination with additional therapeutic agents.

In one embodiment, the compounds of the present disclosure are administered in therapeutically effective amount, whether alone or as a part of a pharmaceutical composition. The therapeutically effective amount and the dosage administered will, of course, vary depending upon known factors, such as the pharmacodynamic characteristics of the particular agent and its mode and route of administration, the age, health and weight of the recipient; the severity and stage of the disease state or condition; the kind of concurrent treatment; the frequency of treatment; and the effect desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

In these pharmaceutical compositions, the compound(s) of the present disclosure will ordinarily be present in an amount of about 0.5-95% weight based on the total weight of the composition. Multiple dosage forms may be administered as part of a single treatment.

The active agent can be administered enterally in solid dosage forms, such as capsules, tablets, and powders, or in liquid dosage forms, such as milk, elixirs, syrups and suspensions. It can also be administered parenterally, in sterile liquid dosage forms. The compound(s) of the present disclosure can also be administered intranasally (nose drops) or by inhalation via the pulmonary system, such as by propellant based metered dose inhalers or dry powders inhalation devices. Other dosage forms are potentially possible such as administration transdermally, via patch mechanism or ointment.

Formulations suitable for enteral or oral administration may be liquid solutions, such as a therapeutically effective amount of the compound(s) dissolved in diluents, such as milk, water, saline, buffered solutions, infant formula, other suitable carriers, or combinations thereof. The compound(s) can then be mixed to the diluent just prior to administration. In an alternate embodiment, formulations suitable for enteral or oral administration may be capsules, sachets, tablets, lozenges, and troches. In each embodiment, the formulation may contain a predetermined amount of the compound(s) of the present disclosure, as solids or granules, powders, suspensions and suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 50% by weight of the compound(s) in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The compound(s) of the present disclosure can be formulated into aerosol formulations to be administered via nasal or pulmonary inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The compound(s) of the present disclosure, alone or in combination with other suitable components, may be administered in an aqueous solution as a nasal or pulmonary spray and may be dispensed in spray form by a variety of methods known to those skilled in the art. Systems for dispensing liquids as a nasal spray are disclosed in U.S. Pat. No. 4,511,069. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the active agent dissolved or suspended in a pharmaceutical solvent, e.g., water, ethanol, or a mixture thereof.

Nasal and pulmonary solutions of the present invention typically comprise the drug or drug to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally between about pH 3.0 and 6.0, preferably 4.5.+−.0.5. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, chlorobutanol, benzylalkonium chloride, and the like. Suitable surfactants include, but are not limited to, oleic acid, sorbitan trioleate, polysorbates, lecithin, phosphatidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, nasal and pulmonary formulations are administered as dry powder formulations comprising the active agent in a dry, usually lyophilized, form of an appropriate particle size, or within an appropriate particle size range, for intranasal delivery. Minimum particle size appropriate for deposition within the nasal or pulmonary passages is often about 0.5 μm. mass median equivalent aerodynamic diameter (MMEAD), commonly about 1 μm MMEAD, and more typically about 2 μm MMEAD. Maximum particle size appropriate for deposition within the nasal passages is often about 10 μm MMEAD, commonly about 8 μm MMEAD, and more typically about 4 μm MMEAD. Intranasally and pulmonarily respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which relies on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

To formulate compositions for nasal or pulmonary delivery, the active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for nasal or pulmonary delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

The compound(s) of the present disclosure may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters, etc. can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the active agent.

The compounds of the present disclosure may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic pharmaceutically acceptable carriers can be used which include, for example, pharmaceutical grades of mannitol, lactose, starch, magnesium stearate, sodium saccharin, talcum, magnesium carbonate, and the like.

Compositions of the present disclosure can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants.

In certain embodiments, compound(s) and compositions of the present disclosure are administered in a time-release formulation, for example in a composition which includes a slow release polymer. Such compositions can be prepared with carriers that will protect against rapid release, for example a controlled release vehicle such as a polymer, microencapsulated delivery system or bioadhesive gel. Prolonged delivery, in various compositions of the invention can be brought about by including in the composition agents that delay absorption, for example, aluminum monosterate hydrogels and gelatin. When controlled release formulations is desired, controlled release binders suitable for use in accordance with the invention include any biocompatible controlled-release material which is inert to the active agent and which is capable of incorporating the biologically active agent. Numerous such materials are known in the art.

Formulations suitable for topical administration include creams, emulsions, and gels containing, in addition to the active ingredient, such carriers as are known in the art.

The compounds and compositions of the present disclosure can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Assays

The present disclosure provides a method for identifying a compound effective for treating suboptimal mucociliary clearance and/or increasing airway epithelial cell function in a subject. The present disclosure also provides a method for identifying a compound effective for increasing the activity of the CFTR in a subject. The present disclosure provides a method for identifying a compound effective for increasing a parameter of airway epithelial cell function in a subject in a subject. In one aspect of this embodiment, such parameter is depth of ASL, depth of PCL, CBF, rate of MCT or any combination of the foregoing. In another aspect such parameter is increasing the depth of ASL. In yet another aspect such parameter is increasing the rate of MCT. In still a further aspect, such parameter is increasing the depth of ASL and increasing the rate of MCT. In still a further aspect, such parameter is increasing the depth of ASL, increasing the depth of PCL, increasing CBF, increasing the rate of MCT or a combination of the foregoing.

In each of the foregoing, the subject is free of a congenital or genetic defect in the cellular mucociliary clearance apparatus and/or acquired abnormality in the cellular mucociliary clearance apparatus, including, but not limited to, the CFTR.

Some embodiments of the assay comprise contacting a candidate agent with a cellular system, such as those systems described herein; obtaining a measurement of a property selected from the group consisting of: chloride secretion from the cell, activity of the CFTR, rate of mucous clearance, ASL depth, PCL depth, the rate of CBF and/or rate of MCT; said measuring occurring after the candidate agent is contacted to the cell; comparing the measurement of the property to a baseline value for the property; and identifying the candidate agent as a putative agent if the measurement of the property is significantly greater than the baseline value of the property.

In one embodiment, such a screening assay can be performed, for example, by determining in an appropriate model system (such as, but not limited to, those systems described herein).

Such screening assay may be in vitro, in vivo or ex vivo and may be cell culture based (either with whole cells or lysates) or may be based on an animal model. In one embodiment, the assay utilizes a murine nasal septal epithelial cell or a human sinonasal epithelial cell. In some embodiments, the model system may be a murine nasal septal epithelial cell from a C57 mouse. In further embodiments the model system may be the nasal cavity of a mouse, as described by Cormet-Boyaka et al., *FASEB J.* 23:3743-3751 (2009). In another embodiment, this could by human bronchial epithelial cells. In another embodiment, this could be human, porcine, rat, or murine intact trachea.

The expression of the chloride channel may be measured electrochemically, for example by measuring trans-layer anionic flux in an Ussing chamber.

In one embodiment, the methods involve the identification of candidate or test compounds or agents (polypeptides, functional nucleic acids, carbohydrates, antibodies, small molecules or other molecules) which bind to the chloride channel. Such compounds may then be further tested in appropriate systems (such as, but not limited to, the models systems described herein) to determine the activity of the identified compounds.

Candidate compounds are identified using a variety of assays, such as, but not limited to, assays that employ cells which express the chloride channel (cell-based assays) or in assays with the isolated chloride channel (cell-free assays). The various assays can employ a variety of variants of the chloride channel (for example, full-length, a biologically active fragment, a mutant form of the polypeptide or a fusion protein which includes all or a portion of the desired polypeptide). Moreover, the chloride channel can be derived from any suitable mammalian species (e. g., human, porcine, rat or murine).

If the chloride channel is CFTR, for example, it may be a CFTR from any species, or a known mutation of CFTR from any species. The nucleotide and polypeptide sequences for such versions of CFTR are available to those skilled in the art on public databases, such as Uniprot (www.uniprot.org) and GenBank.

Suitable test compounds for use in the screening assays can be obtained from any suitable source, such as conventional compound libraries. The test compounds can also be obtained using any of the numerous approaches in combinatorial library methods known in the art, including: biological libraries, spatially addressable parallel solid phase or solution phase libraries, synthetic library methods requiring deconvolution, the "one-bead one-compound" library method and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

A screening assay of the disclosure is particularly amenable to a high throughput format, thereby providing a means to screen, for example, a combinatorial library of small organic molecules, peptides, nucleic acid molecules, and the like.

Kits

The present disclosure also provides kits for use in the foregoing methods. In one embodiment, a kit includes a compound of the present disclosure and optionally: (i) one or more delivery systems for such compound; (ii) secondary agents for use in the foregoing methods; and (iii) directions for using the kit (for example, instructions for administration to a subject).

In one embodiment, the compound included in the kit is a CFTR activator. In one embodiment, the CFTR activator is a CFTR potentiator. Known CFTR activators and potentiators include, but are not limited to, are anthracene-9-carboxylic acid (9-Anthroic acid), phloxine B, benzimidazolone analogs NS004 and NS1619, genistein, 7-n-Butyl-6-(4-hydroxyphenyl)[5H]pyrrolo[2,3-b]pyrazine (aloisine A), 2-(2-(1H-indol-3-yl)-N-methylacetamido)-N-(4-isopropyl-phenyl)-2-phenylacetamide (PG01), N-cycloheptyl-6-(N-ethyl-N-phenylsulfamoyl)-4-oxo-1,4-dihydroquinoline-3-carboxamide (SF01), sulfonamide 6-(N-ethyl-N-phenylsulfamoyl)-N-(2-methoxybenzyl)-4-oxo-1,4-dihydroquinoline-3-carboxamide (SF03), capsaicin and curcumin. In one embodiment, the CFTR activator is a compound of the formula I or II.

In one embodiment, the kit contains a label that indicates the contents of the kit are to be administered to a subject suffering from: (i) a neuromuscular disease (such as, but not limited to, muscular dystrophy, spinal muscular atrophy, ALS); (ii) acquired anatomic problem resulting in muscular weakness (which may be associated with conditions, such as, but not limited to, paraplegia, quadriplegia, and diaphragmatic paralysis); (iii) increased prevalence of respiratory infections due to immune deficiency; (iv) excess mucous production (which may be associated with conditions, such as, but not limited to, asthma and asthmaticus); or (v) adverse environmental factors (which may be associated with conditions, such as, but not limited to, smoking or chronic obstructive pulmonary disease).

EXAMPLES

Example 1—CFTR Activators Increase the Activity of WT-CFTR in CFBE41o-Cells

In this example, CFTR activators were examined for the ability to stimulate the anion channel activity of WT-CFTR. Recently the CFTR potentiator ivacaftor was reported to significantly augment cAMP mediated ion transport activity of CFTR encoding the gating mutation G551D-CFTR, in vitro and in CF subjects harboring the G551D-CFTR defect. Ivacaftor improved measures of CFTR activity and also enhanced pulmonary function in CF patients with G551D-CFTR.

Figure 1A:
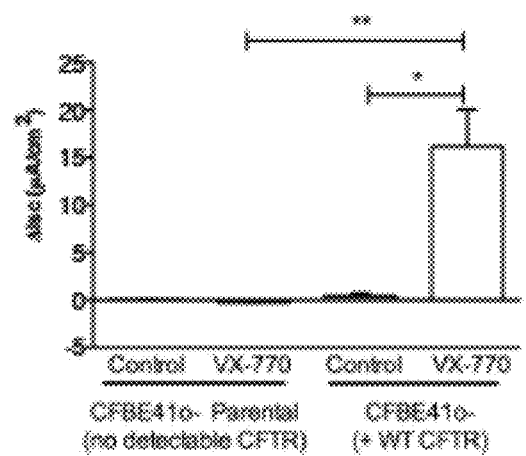
FIGS. 1A-1B show the CFTR potentiator ivacaftor augments wild-type CFTR activity.

The CFTR potentiator ivacaftor was chosen as an exemplary CFTR activator. The activity of ivacaftor was examined in WT-CFTR expressing cells. Ivacaftor induced robust increases in anion transport in CFBE41o-cells (a human normal bronchiolar epithelial cell line) complemented with stable WT-CFTR expression; no activity was observed in parental cells without detectable CFTR expression, establishing specificity for WT-CFTR (FIG. 1A).

Figure 1B:
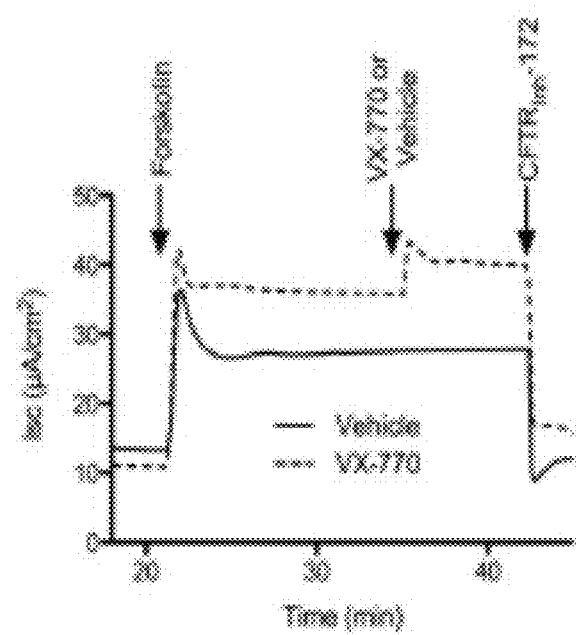

Example 2—CFTR Activators Increase the Activity of WT-CFTR in Primary Human Bronchial Epithelial Cells In primary non-CF human bronchial epithelial (HBE) cells, ivacaftor also augmented CFTR-dependent anion transport activity following pre-stimulation with 100 nM forskolin, a dose chosen to induce cAMP levels matching CSE-exposed cells, increasing CFTR-dependent short-circuit current (Isc) compared to that stimulated by forskolin alone (FIG. 1B).

Example 3—CFTR Activators ASL Depth and MCT in Primary Human Bronchial Epithelial Cells Because CFTR regulates ASL depth, which in turn permits efficient mucociliary clearance, it follows that potentiation of WT-CFTR anion secretion by ivacaftor in bronchial epithelia should also increase ASL depth, resulting in augmented mucus transport compared to unstimulated (resting) conditions.

Figure 2A:
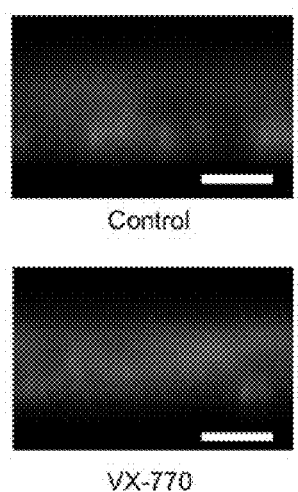
FIGS. 2A-2D show the CFTR potentiator ivacaftor augments ASL depth and increases mucociliary clearance.
Figure 2B:
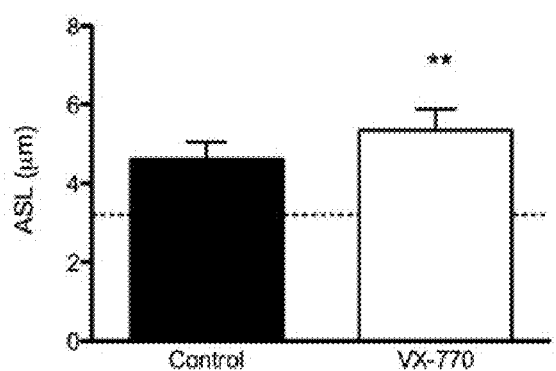
Figure 2C:
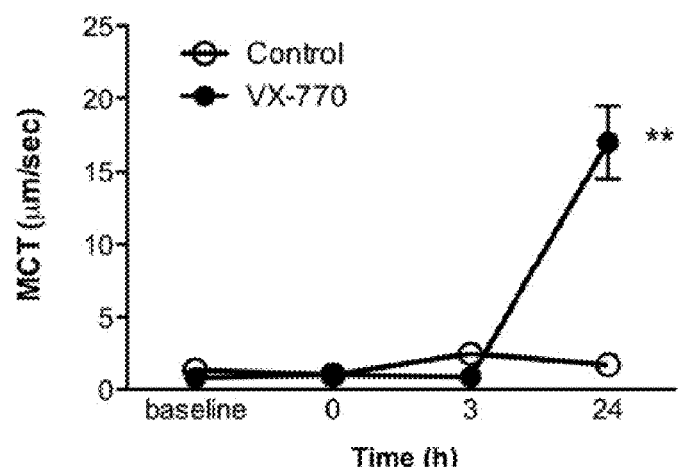
Figure 2D:
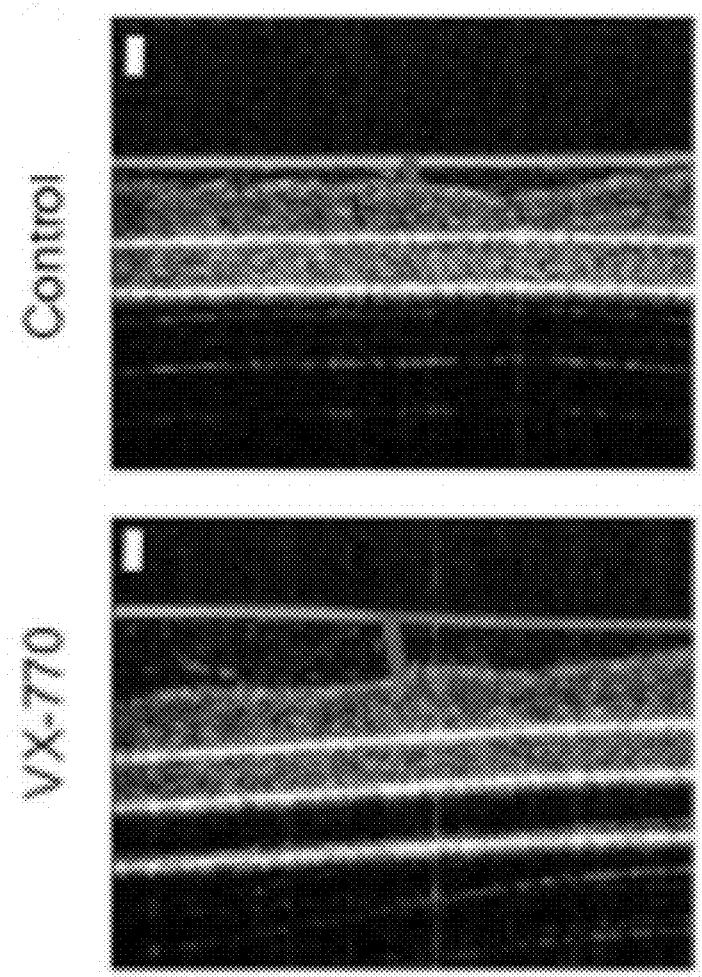

In FIGS. 2A and B, the addition of ivacaftor (10 μM) enhanced ASL depth in HBE monolayers (HBE cells contain WT-CFTR). Moreover, mucus transport (MCT) is markedly increased above baseline in the presence of ivacaftor as compared to control, showing the highly responsive nature of the mucociliary clearance apparatus to alterations in the balance of anion transport and mucus production in healthy WT monolayers (FIG. 2C). The results shown in FIG. 2(C) are further supported by reports that inhaled hypertonic saline augments MCT among healthy individuals. These changes are readily apparent by μOCT monitoring and indicate robust enhancement of MCT in WT epithelia by ivacaftor (FIG. 2D).

Example 4—CFTR Activators Increase the Activity of WT-CFTR in Normal Explanted Human Trachea Ivacaftor also potentiated CFTR-dependent current in normal explanted human trachea examined under voltage clamp conditions (FIGS. 3A and B).

Example 5—CFTR Activators Increase Mucociliary Transport in Primary Human Bronchial Epithelial Cells as Evaluated Using μOCT As discussed above, relevant metrics for evaluation of the mucociliary apparatus include the airway surface liquid (ASL) depth, the thickness of the thin layer of liquid surrounding the cilia known as the periciliary liquid (PCL) depth, the ciliary beat frequency (CBF), and the velocity of mucociliary transport (MCT). μOCT imaging allows the direct and simultaneous measurements of ASL, PCL, MCT, ciliary stroke pattern and CBF without exogenous labeling or direct contact, providing a new tool to interrogate the functional microanatomy of respiratory epithelia with unequaled resolution.

The effect of CFTR activators was evaluated using μOCT imaging in HBE cells (FIGS. 4A-4D). The epithelial monolayer and the cilia can be visualized with a resolution comparable to medium power histology. Mucus and the PCL layer that together comprise the airway surface liquid (ASL) layer can also be clearly visualized. As shown in FIGS. 4A-4D, from top to bottom, the air has no μOCT signal, while the mucus layer appears heterogeneous with high μOCT signal intensity. The PCL gel has a low μCT signal intensity compared with the mucus and monolayer and includes ciliary structures. The air-liquid interface, mucus-PCL interface, and apical cell surface are clearly defined so that ASL and PCL heights can be directly measured with submicrometer resolution. In addition to the different layers, cilia tips can be readily detected by μOCT, as they are brighter than the surrounding PCL and mucus. The tips maintain contact with the deep surface of mucus blanket and lift the mucus nearby by a few hundred nanometers during the effective stroke.

Figure 4A:
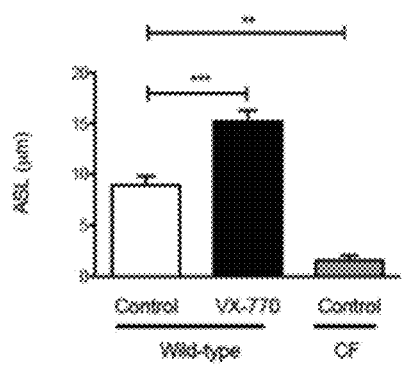
Figure 4B:
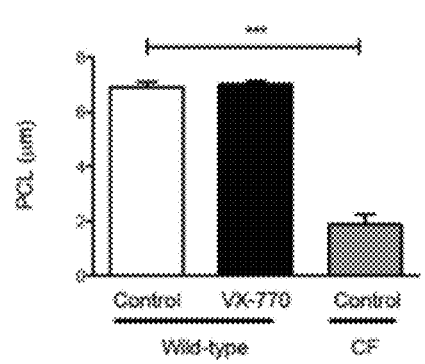
Figure 4C:
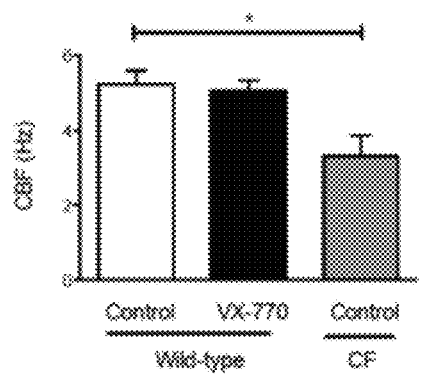
Figure 4D:
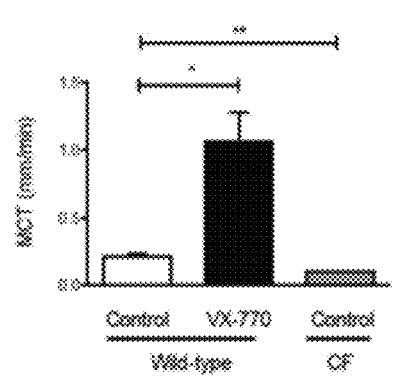

The results in this example, illustrated in FIGS. 4A-4D, confirm the results shown above that CFTR activators increase the activity of WT-CFTR. In FIGS. 4A-4D, control HBE cells containing a defective CFTR (designated control, CF) were used along with HBE cells containing a WT-CFTR (designated control and VX-770, wild-type). Control cells received vehicle alone (0.2% DMSO); ivacaftor was used in all cases at 10 μM. In FIG. 4A, ivacaftor increased ASL depth significantly above control in control wild-type and control CF HBE cells. PCL depth and CBF were not increased in a statistically significant manner by ivacaftor addition in comparison to control wild-type but was increased as compared to control CF HBE cells (FIGS. 4B and 4C). In terms of PCL depth, the PCL only extends approximately 7 microns (corresponding to the depth of the full length cilia); further increases are difficult to detect. For CBF, the rate of CBF may not be rate limiting in all conditions. For example, if the cilia were beating against thick mucus (caused for example by mucus overproduction or the inability to clear mucus normally), the CBF would be slower. However, in this assays the determination of CBF is made versus a normal control making meaning an increase in CBF may not be detected in all cases. Importantly, overall MCT was increased significantly in ivacaftor treated cells as compared to control wild-type and control CF cells.

FIGS. 5A-5D show similar results using HBE cells containing WT-CFTR and further shows the ability of CFTR activators to increase CFTR activity in the presence of environmental insults (in this example, cigarette smoke extract, CSE). Data in FIGS. 5A-5D are derived from 5 measurements per well, with three wells per condition. In FIGS. 5A-5D, all cells contained WT-CFTR; control cells received DMSO vehicle (2.2% DMSO), CSE indicates cells received 2% CSE extract administered apically; CSE indicates cells received 2% CSE extract administered apically and 10 μM ivacaftor administered basolaterally; VX-770 indicates cells received 10 μM ivacaftor administered basolaterally. All data were derived from μOCT images as described herein.

FIG. 5A show μOCT images for each condition; ASL depth is indicated by the dark bar (white bar is for scale and equals 10 microns). FIGS. 5B, 5C and 5D show ASL depth, CBF and MCT, respectively, for the 4 conditions. As shown in FIG. 5B, HBE cells exposed to CSE has decreased ASL depth as compared to control cells; addition of ivacaftor significantly increased ASL depth. Furthermore, addition of ivacaflor alone also significantly increased ASL depth as compared to control. Similar trends were seen with CBF (FIG. 5C). MCT is shown in FIG. 5D. The addition of CSE decreased MCT to almost undetectable levels as compared to control cells; again, addition of ivacaftor increased MCT to that seen in the control cells. Addition of ivacaftor alone also significantly increased MCT as compared to control.

Example 6—CFTR Activators Increase Mucociliary Transport in Human Bronchial Tissue as Evaluated Using μOCT To further investigate the role of CFTR activators in modulating airway epithelial cell function, CFTR activators were studied in combination with human bronchial tissue from a failed healthy donor. Human bronchial tissue was obtained and maintained as described herein. Control experiments were performed with the human bronchial tissue being exposed to DMSO control only (0.2%) and compared to ivacaftor treatment. The results are shown in FIGS. 6A-6C. FIGS. 6A-6C show ASL depth, CBF and MCT, respectively. As illustrated in FIG. 6A, ivacaftor (10 μM) treatment significantly increased ASL depth. In control cells, ASL depth was approximately 10 microns; ivacaftor treatment increased ASL depth to approximately 30 microns. Likewise CBF frequency was also significantly increased in the presence of ivacaftor (10 μM) (FIG. 6B). Finally, MCT was also significantly increased after ivacaftor treatment (10 μM) (FIG. 6C; form a control value of less than 0.01 mm/min to almost 0.04 mm/min).

Example 7—CFTR Activators Increase Mucociliary Transport in Porcine Trachea as Evaluated Using μOCT To further investigate the role of CFTR activators in modulating airway epithelial cell function, CFTR activators were studied in combination with porcine trachea. In this example, porcine trachea from animals having a mutated CFTR (CFTR (−/−) and from animals having a WT-CFTR (CFTR+/+) were evaluated for ASL depth, PCL depth, CBF and MCT. The results are shown in FIGS. 7A-7H.

FIGS. 7A and 7B show representative μOCT images for a CFTR−/− (FIG. 7A) and CFTR+/+(FIG. 7B) animal; ASL depth is indicated by the dark bar with the light bar representing a scale bar of 10 microns. FIGS. 7C-7F, respectively, show ASL depth, PCL depth, CBF and MCT measurements derived from μOCT images from CFTR−/− and CFTR+/+ animals. As can be seen, ASL and PCL depth was significantly decreased in the CFTR−/− animals as compared to the CFTR+/+ animals. Furthermore, CBF frequency and MCT were also significantly decreased in the CFTR−/− animals as compared to the CFTR+/+ animals.

FIGS. 7G and 7H show the response of epithelial functional parameters, namely ASL depth, CBF and MCT in CFTR−/− and CFTR+/+ animals in response to sequential pharmacologic intervention by ivacaftor (10 μM), forskolin (100 nM) and acetylcholine (100 μM); in this experiment, acetylcholine served as a positive control to induce glandular extrusion in CF tissue). In these experiments, agonists were added to the bath solution and all experiments were conducted under physiological conditions (37° C. and 100% humidity). As can be seen in FIG. 7G, no response to ivacaftor or forskolin treatment in terms of ASL depth, CBF or MCT was observed; a positive response to acetylcholine was observed in this tissue as expected. In contrast to FIG. 7G, ASL depth, CBF and MCT were all increased in response to ivacaftor treatment in CFTR+/+ animals, consistent with the results described above for human tissue.

Materials and Methods

Procurement and Growth of Primary Airway Epithelial Cells

Use of human cells and tissues was approved by the UAB Institutional Review Board.

Primary human bronchial epithelial (HBE) cells were derived from lung explants after written informed consent was obtained from CF and non-CF subjects with confirmed CFTR genetics by methods described previously. Briefly, tissues were debrided immediately after surgical resection, washed twice in Minimum Essential Media (MEM) with 0.5 mg/ml DTT (Sigma-Aldrich, St. Louis, Mo.) and 25 U/ml DNAse I (Roche, Basel, Switzerland), and then placed in dissociation media containing MEM, 2.5 U/ml DNAse I, 100 μg/ml ceftazidime, 80 μg/ml tobramycin, 1.25 μg/ml amphotericin B, and 4.4 U/ml pronase (Sigma-Aldrich) for 24-36 h at 4° C. Loosened airway epithelial cells were then expanded in growth media containing BEGM (LONZA, Basel, Switzerland) supplemented with an additional 10 nM all trans-retinoic acid (Sigma-Aldrich) that was exchanged every 24 h. Following expansion, first or second passage cells were seeded on permeable supports for studies.

Once 80-90% confluent, cells were seeded on Snapwell 1.13 cm2 permeable supports (1×106 cells/filter; Bayer, Pittsburgh, PN) or Costar 0.4 μm permeable supports (5×105 cells/filter; Bethesda, Md.) after coating with NIH 3T3 fibroblast conditioned media, and grown in differentiating media containing DMEM/F12 (Invitrogen, Carlsbad, Calif.), 2% Ultroser-G (Pall, New York, N.Y.), 2% Fetal Clone II (Hyclone, Logan, Utah), 2.5 μg/ml Insulin (Sigma-Aldrich), 0.25% bovine brain extract (LONZA), 20 nM hydrocortisone (Sigma-Aldrich), 500 nM Triodothyronine (Sigma-Aldrich), 2.5 μg/ml transferrin (Invitrogen), 250 nM ethanolamine (Sigma-Aldrich), 1.5 μM epinephrine (Sigma-Aldrich), 250 nM phosphoetheanolamine (Sigma-Aldrich), and 10 nM all trans-retinoic acid until terminally differentiated, as previously described (1, 2).

Procurement and Growth of Normal Piglet Trachea

Normal piglet tracheas were obtained from Exemplar Genetics (Sioux Center, Iowa). Tissue were dissected from one-day-old piglets and shipped on wet ice in DMEM. A modified protocol based on airway tissue handling and preparation methods developed by Ballard et al. (Am J Physiol Lung Cell Mol Physiol 298: L270-276, 2010) was employed. Tracheas were immersed in 80 mL Ringer bicarbonate solution (KRB) baths at room temperature and slowly warmed to 37° C. After four hours of pretreatment, the tracheas were removed from the KRB. Accessible mucus and liquid were aspirated from the airway lumens and the tracheal ends were cannulated so that the serosal surface was bathed in KRB [29] without contacting the mucosal surface, as previously described (Ballard et al., Am J Physiol Lung Cell Mol Physiol 298: L270-276, 2010; Martens, et al., Am J Physiol Lung Cell Mol Physiol 301: L236-246, 2011). Tracheas were allowed to equilibrate in KRB bubbled with 95% 02 and 5% CO2 at 37° C. and the luminal side exposed to conditioned air at 100% humidity for 2 hours prior to mOCT imaging (Sleigh et al., Comp Biochem Physiol A Comp Physiol 94: 359-364, 1989).

Procurement and Growth of Normal Human Trachea

Samples of human trachea tissue were obtained from normal donor explant organs not selected for lung transplantation. Lung, mainstem bronchi, and trachea were resected en-bloc, transferred on wet ice, and large airways excised. Airway tissues were then immersed in ice cold DMEM following resection for transfer, then allowed to equilibrate to room temperature prior to mOCT imaging.

Micro Optical Coherence Tomography (μOCT) Studies

The μOCT system is a spectral-domain OCT implementation with several improvements to standard OCT that yield high resolution in both lateral and axial directions. The general layout and axial resolution characterization have been described (Liu et al., PLOSOne, 8(1), E54473-2013). A super-continuum source (Fianium SC450) provides the high-bandwidth, short coherence length light necessary for high axial resolution (1.3 mm). A typical OCT system includes an interferometer with the reference and sample arms intersecting at a beamsplitter. The beamsplitter is replaced in μOCT with a 45 degree rod mirror, which apodizes the sample beam by introducing a circular obscuration in the center to achieve a balance of good lateral resolution (2 μm) and long depth of focus (0.2 mm). Custom software is employed to control the galvanometer scanning motors while acquiring spectral data from the line camera. The system operates with user-configurable line and frame rates and customizable scan geometry; typical settings are 32 or 40 frames per second, 512 A-lines per frame in a linear scan, and 0.5 mm by 0.5 mm (X by Z) for a cross-sectional image. The effective thickness of each cross-section is equal to the μOCT beam spot size (2 μm).

μOCT imaging was performed on various cells cultures with illumination incident on the apical side of the cells. The axis of the imaging optics is typically placed within 10 degrees of normal to the cell plane to minimize errors in geometric measurements. ASL and PCL were measured directly from the thicknesses of the visible layers in the image with a correction applied for the index of refraction in the liquid (n=1.33). ASL and PCL were evaluated at 5 equally distributed regions of the image. CBF and MCT were determined from a time series of images. CBF was measured by finding the frequency of peak amplitude in the temporal Fourier transform of the regions exhibiting oscillatory behavior. Up to 10 regions of ciliary activity per image sequence were assessed for CBF. MCT was computed by measuring the displacement of 5 to 10 visible inclusions in the mucus through time. All image analysis was performed with ImageJ and Matlab. Analysis for various tissue explants was performed in a similar manner.

Voltage Clamp Studies in Ussing Chambers

Short-circuit current (Isc) was measured under voltage clamp conditions using MC8 voltage clamps and P2300 Ussing chambers (Physiologic Instruments, San Diego, Calif.) as previously described (2). Monolayers were initially bathed on both sides with identical Ringer's solutions containing (in mM) 115 NaCl, 25 $NaHCO_3$, 2.4 $KH_2PO_4$, 1.24 $K_2HPO_4$, 1.2 $CaCl_2$, 1.2 $MgC_2$, 10 D-glucose (pH 7.4). Bath solutions were vigorously stirred and gassed with 95%02:5% CO2. Short-circuit current measurements were obtained using an epithelial voltage clamp (Physiologic Instruments). A one-second three-mV pulse was imposed every 10 seconds to monitor resistance calculated using Ohm's law. Where indicated, the mucosal bathing solution was changed to a low Cl-solution containing 1.2 NaCl and 115 Na+ gluconate, and all other components as above. Amiloride (100 μM) was added to block residual Na+ current, followed by the agonists forskolin, ivacaftor, and ATP as indicated (minimum five-min observation at each concentration). CFTRInh-172 (10 μM) was added to the mucosal bathing solution at the end of experiments to block CFTR-dependent Isc. All chambers were maintained at 37° C., and agonist stimulation was initiated within 15 min of placement into the chambers.

Mucus Transport Studies

HBE cells were washed with sterile PBS twice 1-2 days prior to addition of PEG beads. Fifty (50) μl of Diamine polyethylene glycol (PEG) coated fluorescent beads (1 μm, Molecular Probes, Eugene, Oreg., 1:500 dilution in PBS) were added to the apical surface by using a microsprayer aerosolizer (Penn-Century Inc Model IA-1B, Wyndmoor, Pa.). Following 24 h incubation, baseline images were obtained and then test compounds added to the basolateral compartment. Mucociliary transport (MCT) images were captured by time-lapse fluorescence imaging at four regions of interest per well located 1 mm from the periphery of the well and at each quadrant using an inverted epifluorescence microscope (Nikon Diaphot, Melvin, N.Y.; 488 nm excitation/519 nm emission). Linear transport rates were computed using Metamoph 7.0 by analyzing 10-15 particles per region (7).

Airway Surface Liquid (ASL) Depth Measurement by Confocal Microscopy

The apical surfaces of HBE cells were washed three times and then test compounds added to the basolateral compartment 24 h prior to labeling. Cells were stained with CMFDA (100 μM) in the cell culture medium for 1 hr. Texas red dye (25 μl at 2 mg/ml in Fc70) was added apically and cells allowed to equilibrate 2 h at 37° C. Transwell membranes were placed in sterile glass bottom dish coated with MEM, and imaged with a Carl Zeiss (Peabody, Mass.) confocal microscope using 20× (numerical aperture 0.88, working distance 0.55 mm) air objective lens. Cells were visualized with DIC optics to evaluate cell morphology before initiating fluorescence microscopy. Subsequently, Zscan confocal fluorescent microscopy images were acquired from the top of the ASL through the top of the cell surface. XZ scans were analyzed using Zen2008 software at four ROI per well each located 1 mm from the filter periphery and at each quadrant; 5 estimates of ASL depth were taken equally dispersed across each ROI (7, 9).

Statistics

Descriptive statistics (mean, SD, and SEM) were compared using Student's t-test or ANOVA, as appropriate. Post-hoc tests for multiple comparisons following ANOVA were calculated using Fisher's least significant difference. All statistical tests were two-sided and were performed at a 5% significance level (i.e., α=0.05) using GraphPad Prism (La Jolla, Calif.). Error bars designate SEM unless indicated otherwise. Correlation analysis was performed using SPSS (IBM, Armonk, N.Y.).

What is claimed:

1. A method for increasing a parameter selected from the group consisting of: (i) a depth of airway surface liquid, (ii) a depth of periciliary liquid, (iii) ciliary beat frequency (CBF) or (iv) a combination of the foregoing in a subject, the method comprising the step of administering to the subject a compound of the formula I:

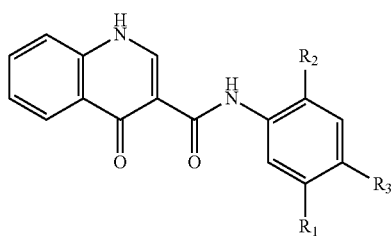

I wherein:
$R_1$ is =O, OH or H; and
$R_2$ and $R_3$ are each independently, H, OH or substituted or unsubstituted C1-C7 alkyl, and wherein the subject is free from congenital or genetic defect in the CFTR.

2. The method of claim 1, wherein the subject is further free from a congenital or genetic defect in the cellular mucociliary clearance apparatus, an acquired abnormality in the cellular mucociliary clearance apparatus or a combination of the foregoing.

3. The method of claim 1, wherein the subject is free an acquired abnormality in the CFTR.

4. The method of claim 1, wherein the compound of formula I has the structure:

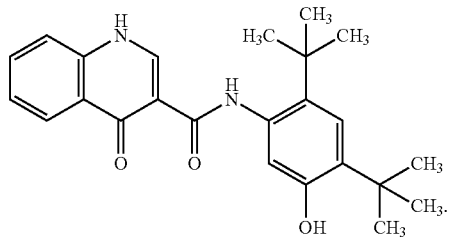 [SMILES: CC(C)(C)c1cc(C(C)(C)C)c(NC(=O)c2c[nH]c3ccccc3c2=O)cc1O]

5. The method of claim 1, wherein the parameter is the depth of airway surface liquid and the depth of periciliary liquid.

6. The method of claim 1, wherein the parameter is the depth of airway surface liquid and the ciliary beat frequency.

7. The method of claim 1, wherein the parameter is the depth of periciliary liquid and ciliary beat frequency.

8. The method of claim 1, wherein said administering increases the depth of airway surface liquid.

9. The method of claim 8, wherein the subject is free from the congenital or genetic defect in the CFTR and is free from the acquired abnormality in the CFTR.

10. The method of claim 1, wherein said administering increases the depth of periciliary liquid.

11. The method of claim 10, wherein the subject is free from the congenital or genetic defect in the CFTR and is free from the acquired abnormality in the CFTR.

12. The method of claim 1, wherein said administering increases ciliary beat frequency.

13. The method of claim 12, wherein the subject is free from the congenital or genetic defect in the CFTR and is free from the acquired abnormality in the CFTR.

14. The method of claim 1, wherein the subject has a wild-type CFTR.

15. The method of claim 1, wherein the compound of formula I is administered in a therapeutically effective amount.

16. The method of claim 4, wherein the compound of formula I is administered in a therapeutically effective amount.

* * * * *

UNITED STATES PATENT AND TRADEMARK OFFICE
CERTIFICATE OF CORRECTION

PATENT NO. : 10,300,052 B2
APPLICATION NO. : 15/582260
DATED : May 28, 2019
INVENTOR(S) : Steven M. Rowe and Mark Dransfield It is certified that error appears in the above-identified patent and that said Letters Patent is hereby corrected as shown below:

In the Specification

In Line 3 please Insert the following paragraph following the title:
--STATEMENT AS TO FEDERALLY SPONSORED RESEARCH
This invention was made with government support under grant number HL105487 awarded by the National Institutes of Health. The government has certain rights in the invention.--

Signed and Sealed this
Eighth Day of October, 2019

Andrei Iancu
*Director of the United States Patent and Trademark Office*